United States Patent [19]
Hagiwara et al.

[11] Patent Number: 5,356,749
[45] Date of Patent: Oct. 18, 1994

[54] IMAGING METHOD COMPRISING A DEVELOPER HAVING A NOVEL GUANIDINE TYPE COMPOUND

[75] Inventors: Kazuyoshi Hagiwara; Katsuhiko Tanaka, both of Yokohama, Japan

[73] Assignee: Canon Kabushiki Kaisha, Tokyo, Japan

[21] Appl. No.: 79,826

[22] Filed: Jun. 23, 1993

Related U.S. Application Data

[62] Division of Ser. No. 599,499, Oct. 18, 1990, Pat. No. 5,246,810.

[30] Foreign Application Priority Data

Oct. 18, 1989 [JP] Japan .................. 1-269070

[51] Int. Cl.$^5$ ............................. G03G 13/08
[52] U.S. Cl. ........................... 430/122; 430/120
[58] Field of Search ............... 430/110, 106, 106.6, 430/109, 120, 122

[56] References Cited

U.S. PATENT DOCUMENTS

| | | | |
|---|---|---|---|
| 1,953,494 | 4/1934 | Meis | 260/125 |
| 2,297,691 | 10/1942 | Carlson | 95/5 |
| 3,320,229 | 5/1967 | Szabo et al. | 260/96.5 |
| 3,607,261 | 9/1971 | Amidon et al. | 96/1.8 |
| 3,666,363 | 5/1972 | Tanaka et al. | 355/17 |
| 4,071,361 | 1/1978 | Marushima | 96/1.4 |
| 4,663,263 | 5/1987 | Ikeda et al. | 430/110 |
| 5,084,369 | 1/1992 | Tanaka et al. | 430/110 |

FOREIGN PATENT DOCUMENTS

| | | | |
|---|---|---|---|
| 0066470 | 12/1982 | European Pat. Off. | G03G 9/08 |
| 0178952 | 4/1986 | European Pat. Off. | G03G 9/08 |
| 0179642 | 4/1986 | European Pat. Off. | G03G 9/08 |
| 0423756 | 4/1991 | European Pat. Off. | |
| 4223910 | 11/1976 | Japan . | |
| 4324748 | 2/1978 | Japan . | |
| 59-195166 | 3/1985 | Japan . | |
| 63-05357 | 1/1988 | Japan | G03G 9/10 |
| 63-216062 | 9/1988 | Japan | G03G 9/08 |

OTHER PUBLICATIONS

Ram, V. J.; Pancley, H. N., Singh, S. N. Indian J. Pharm. 35(1) 1973, 30–32.
Josh, PC, Parmar S. S., Indian J. Pharm. Sc. 40(5), 1978, 161–163.
Chem. Abstracts, Abst. 78 (17) 110817g.
Chem. Abstracts, Abst. 90 (15) 114915r.

*Primary Examiner*—Marion E. McCamish
*Assistant Examiner*—Rosemary Ashton
*Attorney, Agent, or Firm*—Fitzpatrick, Cella, Harper & Scinto

[57] ABSTRACT

A guanidine type compound has the following formula:

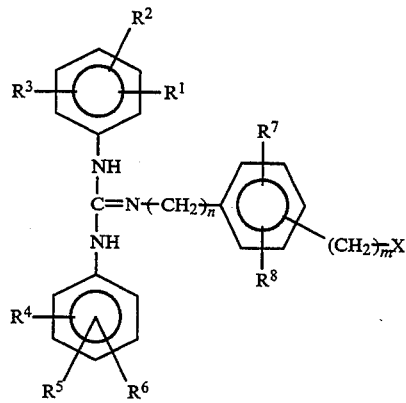

wherein $R^1$ to $R^8$ are each a hydrogen atom, an alkyl group, an amino group, an alkoxy group, a substituted or unsubstituted aryl group, and $R^1$ to $R^8$ may be the same as or different from each other and together may form a ring with the adjacent substituents; X is a halogen atom, a hydroxyl group or an alkoxy group; and m and n are each an integer having a value of 1 to 8. The guanidine compound is employed in a toner for electrostatic development and the toner can be used in an electrophotographic apparatus including a facsimile apparatus for receiving image information from an electrophotographic copier.

27 Claims, 2 Drawing Sheets

IMAGING METHOD COMPRISING A DEVELOPER HAVING A NOVEL GUANIDINE TYPE COMPOUND

This application is a division of application Ser. No. 07/599,499 filed Oct. 18, 1990, now U.S. Pat. No. 5,246,810.

BACKGROUND OF THE INVENTION

Field of the Invention and Related Art

The present invention relates to a guanidine type compound for developing electrostatic images and a toner having the guanidine compound. The present invention also relates to a developer containing the toner for developing electrostatic images. The present invention further relates to an apparatus unit which is detachably provided on the apparatus body and which comprises a developing means having the toner or the developer for developing electrostatic images and a body to be charged, both of which are integrally supported to form the unit. The present invention still further relates to an electrophotographic apparatus having a developing means, which holds the toner or the developer for developing electrostatic images, and to a facsimile apparatus which uses as a printer the electrophotographic apparatus.

Various electrophotographic methods have been disclosed in, for example, U.S. Pat. No. 2,297,691 and Japanese Patent Publication Nos. 42-23910 and 43-24748.

The developing methods applied to the electrophotographic methods are roughly classified into a dry developing method and a wet developing method. The dry developing method is further divided into a method using a two-component developer and a method using a one-component developer.

Fine powder of natural or synthetic resins in which a dye or pigment is dispersed is used as a toner applied to the dry developing method. For example, particles having sizes ranging from 1 to 30 μm, which are obtained by pulverizing a binder resin such as polystyrene in which a coloring agent is dispersed, are used as the toner which is used as the one-component developer. Particles containing a magnetic material such as magnetite are used as a generally known magnetic toner. In the case of the method using a two-component developer, the toner used is generally mixed with carrier particles such as glass beads or iron powder.

Both of the above toners must have positive or negative charges corresponding to the polarity of the electrostatic latent image developed.

While the resin component of the toner itself may be charged by frictional electrification, the resins normally used only frictionally electrify to a relatively low level. This results in impeded development with unclear and fogged images. In order to frictionally charge the toner particles to a desired level, a charge applying agent, called a charge controlling agent, is added to the toner.

Examples of charge controlling agents, which are presently known as agents having the property of being positively frictionally charged, include nigrosine dyes, azine dyes, triphenylmethane dyes and pigments, quaternary ammonium salts and polymers having quaternary ammonium salts in side chains thereof.

Since such charge controlling agents easily soil a sleeve or carriers, however, the frictional charge amount of the toner, which contains one of the controlling agents, decreases with an increase in number of the sheets of copying paper used. This causes a decrease in image density.

Since a certain kind of charge controlling agent has the insufficient property of being frictionally charged and is easily affected by temperature and humidity, the agent causes the image density to be changed by an environmental change. In addition, since a certain kind of charge controlling agent has poor dispersibility in resins, the toner containing this agent produces nonuniformity in the frictional charge amount of the toner particles and easily produces fogging. Further, since a certain kind of charge controlling agent has poor preservative stability, the ability to have frictional charges deteriorates during preservation for a long time. A certain kind of charge controlling agent is colored and thus cannot be used in color toners.

In the present situation, therefore, there is a great demand for a charge controlling agent, which removes the above-described problems, and thus such an agent has been developed.

SUMMARY OF THE INVENTION

It is an object of the present invention to provide a novel guanidine type compound which has good dispersibility in resins and which can be used as a charge controlling agent having a high level of ability to have positive charges.

It is another object of the present invention to provide a novel guanidine type compound which has good dispersibility in resins and which is useful as an intermediate for producing a charge controlling agent having a high level of ability to have positive charges.

It is still another object of the present invention to provide a novel guanidine type compound which can be used as a white or a light-colored charge controlling agent which can be used in a color toner having the property of being positively charged.

It is one more object of the present invention to provide a toner which can be used for developing electrostatic images and which contains a novel guanidine type compound which can solve the above-described various problems in electrostatic development.

It is still one more object of the present invention to provide a color toner having a high level of ability to have positive charges and an excellent color tone, having the property of color.

It is another object of the present invention to provide a developer comprising the toner having a novel guandidine compound which can solve the above-described various problems in electrostatic development.

It is still another object of the present invention to provide an electrophotographic apparatus comprising a developing means which holds the toner or the developer which can solve the above-described problems in electrostatic development.

It is one more object of the present invention to provide an apparatus unit which comprises at least a developing means holding the toner or the developer which can solve the above-described various problems in electrostatic development and which is detachably provided on the body of an apparatus.

It is still one more object of the present invention to provide a facsimile apparatus which uses as a printer the electrophotographic apparatus which can solve the abovedescribed various problems in electrostatic development.

It is an additional object of the present invention to provide a guanidine type compound having the following formula:

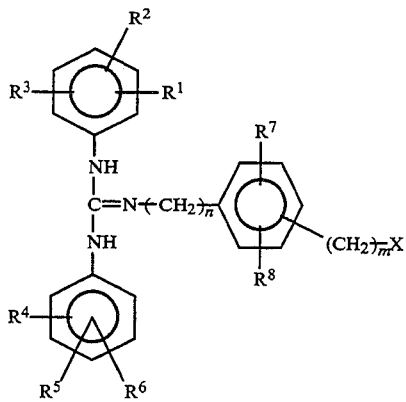

wherein $R^1$ to $R^8$ are each a hydrogen atom, an alkyl group, an amino group, an alkoxy group, a substituted or unsubstituted aryl group, and $R^1$ to $R^8$ are the same as or different from each other an together may form a ring with the adjacent substituents; X is a halogen atom, a hydroxyl group and an alkoxy group; and m and n are each an integer having a value of 1 to 8.

It is an object of the present invention to provide a toner for developing electrostatic images, comprising a binder resin and a guanidine type compound having the following formula:

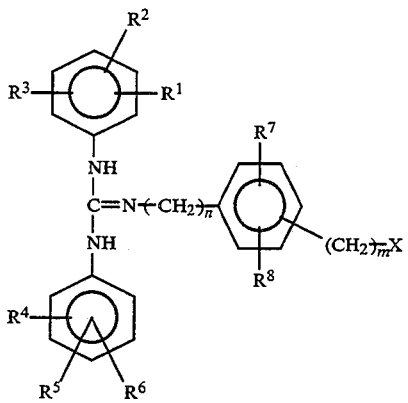

wherein $R^1$ to $R^8$ are each a hydrogen atom, an alkyl group, an amino group, an alkoxy group, a substituted or unsubstituted aryl group, and $R^1$ to $R^8$ may be the same as or different from each other and may form a ring with the adjacent substituents; X is a halogen atom, a hydroxyl group and an alkoxy group; and m and n are each an integer having a value of 1 to 8.

It is an object of the present invention to provide a two-component type developer for developing electrostatic images, comprising a toner and carrier particles, wherein the toner comprises a binder resin and a guanidine type compound having the following formula:

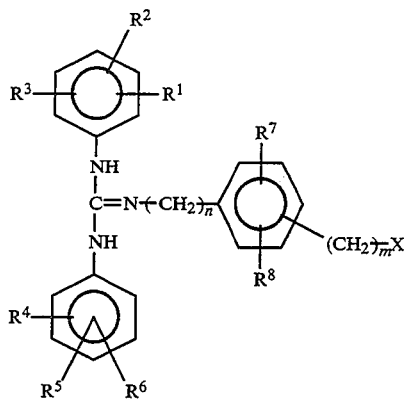

wherein $R^1$ to $R^8$ are each a hydrogen atom, an alkyl group, an amino group, an alkoxy group, a substituted or unsubstituted aryl group, and $R^1$ to $R^8$ may be the same as or different from each other and may together form a ring with the adjacent substituents; X is a halogen atom, a hydroxyl group and an alkoxy group; and m and n are each an integer having a value of 1 to 8.

It is an object of the present invention to provide an apparatus unit comprising: a) a chargeable body for supporting electrostatic images, (b) charging means for charging said chargeable body, and (c) a developing means for developing an electrostatic image supported by said chargeable body, said charging means and said developing means are integrally supported to form a single unit which is detachably provided on the apparatus body, and wherein said developing means includes at least a toner for developing an electrostatic image comprising a binder resin and a guanidine type compound having the following formula:

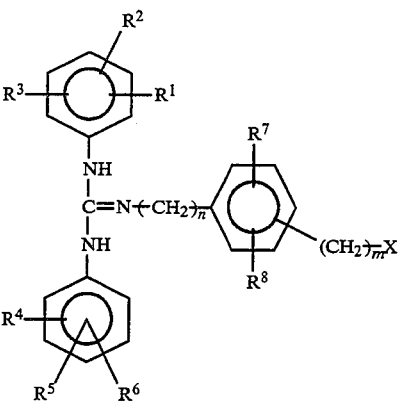

wherein $R^1$ to $R^8$ are each a hydrogen atom, an alkyl group, an amino group, an alkoxy group, a substituted or unsubstituted aryl group, and $R^1$ to $R^8$ may be the same as or different from each other and together may form a ring with the adjacent substituents; X is a halogen atom, a hydroxyl group and an alkoxy group; and m and n are each an integer having a value of 1 to 8.

It is an object of the present invention to provide an electrophotographic apparatus comprising: (a) a chargeable body for supporting electrostatic images, (b) charging means for charging said chargeable body, and (c) developing means for developing an electrostatic image supported by said chargeable body, wherein said developing means includes at least a toner for developing an electrostatic image comprising a binder resin and a guanidine type compound having the following formula:

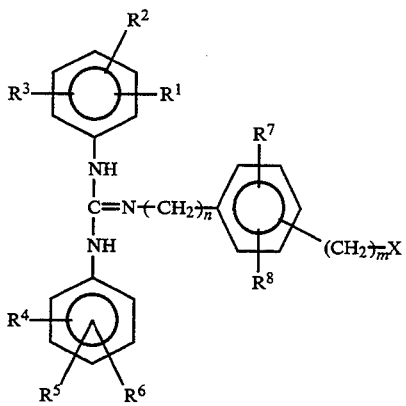

wherein $R^1$ to $R^8$ are each a hydrogen tom, an alkyl group, an amino group, an alkoxy group, a substituted or unsubstituted aryl group, and $R^1$ to $R^8$ may be the same as or different from each other and together may form a ring with the adjacent substituents; X is a halogen atom, a hydroxyl group and an alkoxy group; and m and n are each an integer having a value of 1 to 8.

It is an object of the present invention to provide a facsimile apparatus comprising: (a) electrophotographic imaging means and (b) receiving means for receiving image information from a remote terminal, wherein said electrophotographic imaging means comprises (i) a chargeable body for supporting electrostatic images, (ii) charging means for charging said chargeable body, and (iii) developing means for developing an electrostatic image supported by said chargeable body, wherein said developing means includes at least a toner for developing an electrostatic image comprising a binder resin and a guanidine type compound having the following formula:

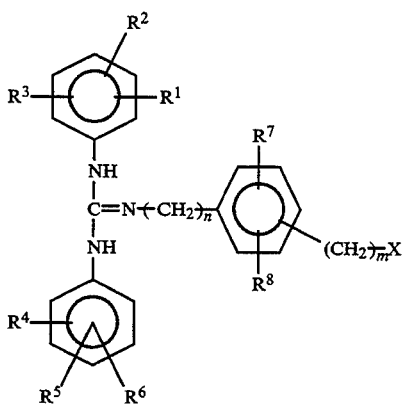

wherein $R^1$ to $R^8$ are each a hydrogen atom, an alkyl group, an amino group, an alkoxy group, a substituted or unsubstituted aryl group, and $R^1$ to $R^8$ may be the same as or different from each other and together may form a ring with the adjacent substituents; X is a halogen atom, a hydroxyl group and an alkoxy group; and m and n are each an integer having a value of 1 to 8.

The novel guanidine type compound of the present invention has the sufficient property of being positively frictionally charged and excellent properties as a charge controlling agent for toners.

DETAILED DESCRIPTION OF THE INVENTION

Figure 1:
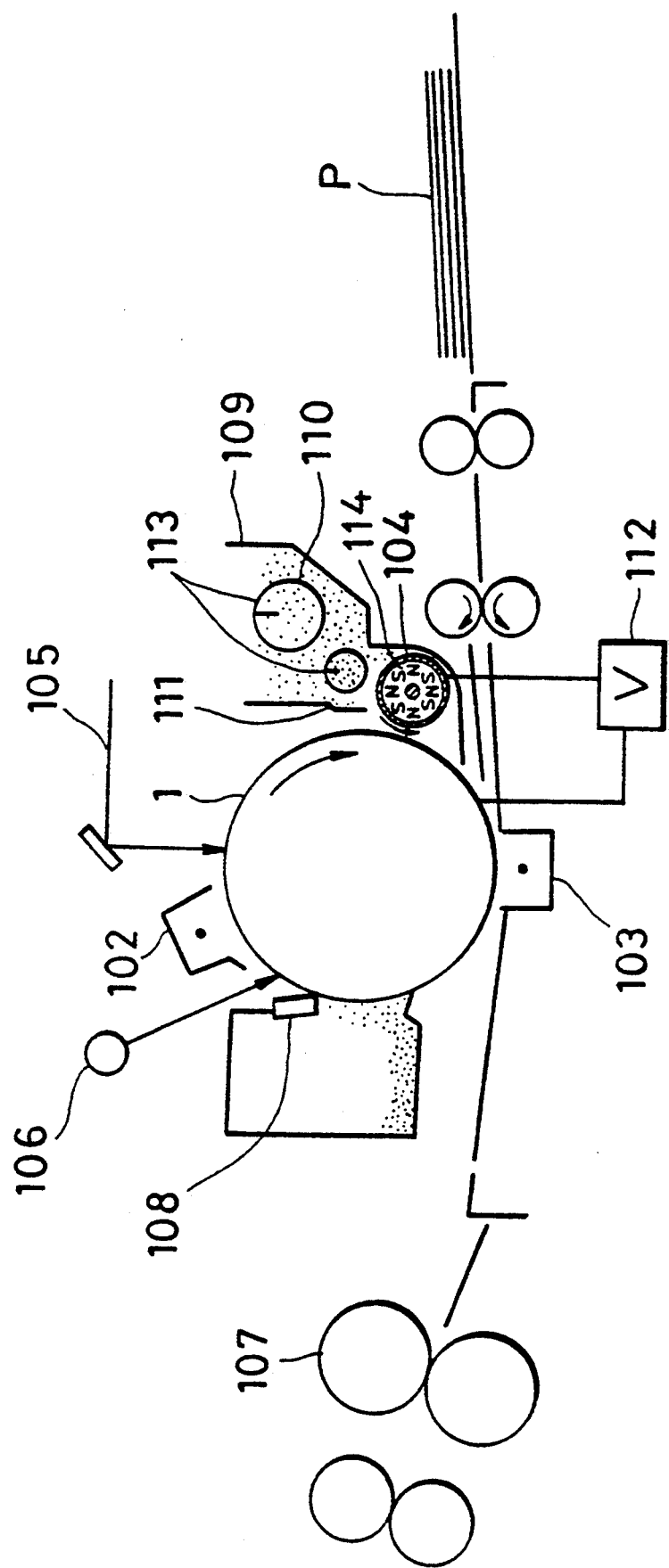
FIG. 1 is a schematic drawing of the arrangement of a general transfer-type electrophotographic apparatus.

The present invention provides a novel guanidine type compound expressed by the following formula (I) or (II):

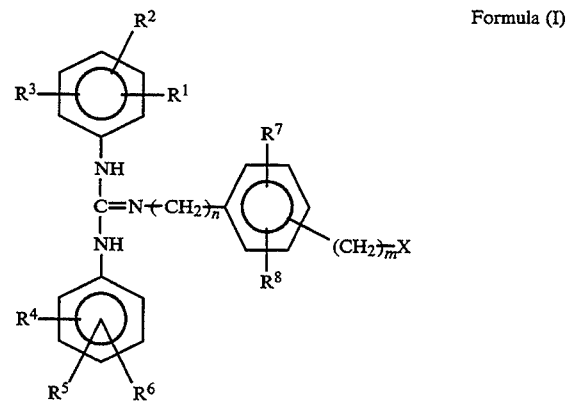

Formula (I)

wherein $R^1$ to $R^8$ are each denote a hydrogen atom, an alkyl group, an amino group, an alkoxy group, a substituted or unsubstituted aryl group, and $R^1$ to $R^8$ may be the same as or different from each other and together may form a ring with the adjacent substituents; X is a halogen atom, a hydroxyl group and an alkoxy group; and m and n are each an integer having a value of 1 to 8.

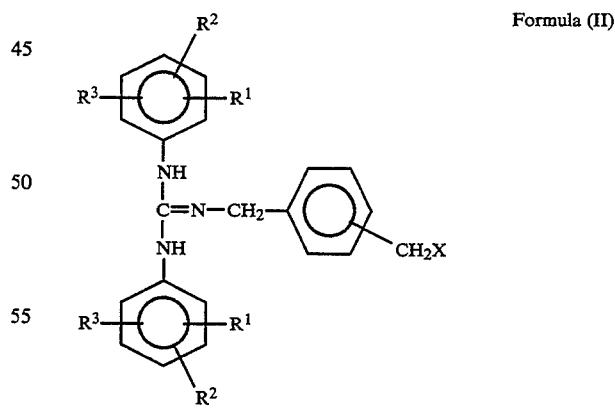

Formula (II)

wherein $R^1$, $R^2$ and $R^3$ are each a hydrogen atom, an alkyl group having 1 to 4 carbon atoms, an alkoxy group having from 1 to 4 carbon atoms or a phenyl group and $R^1$, $R^2$ and $R^3$ may be the same as or different from each other and may form a ring with the adjacent substituents; and X is a halogen atom.

The inventors found that the novel guanidine type compound expressed by the formula (I), preferably (II), in which a substituent having a halogen atom is introduced into each of the nitrogen atoms thereof, has excellent thermal stability and a high level of property of being positively frictionally charged and excellent properties as a charge controlling agent.

Although examples of alkyl groups expressed by $R^1$ to $R^8$ include a methyl group, an ethyl group, a n-propyl group, an isopropyl group, a t-butyl group and a stearyl group, an alkyl group having 1 to 6 carbon atoms is preferable in view of the ease of the synthesis of compound.

Although examples of alkoxy groups include a methoxy group, an ethoxy group, a n-propoxy group, n-butoxy group, a t-butoxy group and a n-pentoxy group, an alkoxy group having 1 to 6 carbon atoms is preferable in view of the ease of the synthesis the compound.

Although examples of amino groups include an amino group, a methylamino group, an ethylamino group, a dimethylamino group, a diethylamino group, a dibutylamino group and a dodecenylamino group, an amino group having 1 to 6 carbon atoms is preferable in view of the ease of the synthesis of the compound.

Examples of aryl groups each of which may have a substituent include a substituted- or unsubstituted phenyl group, tolyl group, xylyl group and naphthyl group. Examples of substituents for the aryl groups include an alkyl group and an alkoxy group. A substituent having 12 carbon atoms or less is preferable in view of the ease of the synthesis of the compound.

When $R^1$ to $R^6$ or $R^7$ and $R^8$ are adjacent, the adjacent substituents may form a ring. For example, aryl groups having substituents $R^1$ to $R^6$ may form a tetrayl group. This applies to an alkyl group, aryl group or alkoxy group expressed by R7 or R8.

Guanidine type compounds have been already known in, for example, U.S. Pat. No., 4,663, 2633 and serve as excellent charge controlling agents. However, since a kind of known guanidine derivative has reactivity between the basic guanidine skeleton and an acid, it cannot be easily applied to a binder resin having a high acid value because the charge amount varies with time. While a guanidine derivative, in which a substituent such as an aryl group, an aralkyl group or an alkyl group is introduced into all the three nitrogen atoms of the basic guanidine skeleton, has low reactivity between the basic guanidine skeleton and an acid due to the influence of steric hindrance of the substituents. This guanidine derivative is thus extremely effective for a case where a binding resin having a high acid value is used. Since the guanidine derivative of the present invention has substituents which are respectively introduced into all the three nitrogen atoms, it has the same effect as that described above. The guanidine derivative of the present invention also permits a further improvement in the good dispersibility in a resin, which is possessed by conventional guanidine derivatives. It is thought that this is caused by the polarity of a portion expressed by X in the formula (I). As a result, since conditions for producing a toner, particularly kneading conditions, can be set to a wide range, many binder resins having different thermal physical properties can be used.

A characteristic of guanidine derivatives is that a toner containing a guanidine derivative has excellent preservative stability and environmental stability, as compared with conventional controlling agents. The guanidine derivatives of the present invention have this characteristic, as well as the above-mentioned characteristics.

The guanidine compound of the present invention is basically obtained by reacting a guanidine derivative with a halogen compound such as xylylene dichloride or xylylene dibromide.

Namely, the guanidine compound of the present invention, in which x is a halogen atom, can be obtained by dissolving a known diaryl guanidine derivative expressed by the following formula (III):

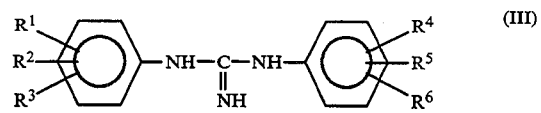

wherein $R^1$ to $R^6$ are each the same as that in the formula (I); and a halogen compound expressed by the following formula (IV) in a molar concentration equal to that of the guanidine derivative:

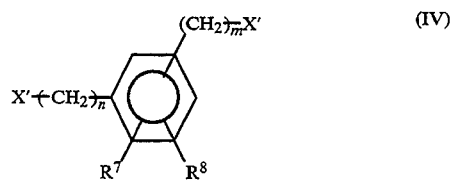

wherein X' is a halogen atom, and n, m, $R^7$ and $R^8$ are each the same as that in the formula (I) in an organic solvent such as toluene, chloroform or dimethylformamide; reacting the thus-formed solution for about 10 hours at the reflux temperature of the solvent used in the presence of a base; removing the catalyst; washing the residue with water; distilling off the solvent; extracting the crystal obtained with an organic solvent such as benzene or acetone; and recrystallizing the crystal. The guanidine compound obtained is further reacted with a hydroxide, an alcohol or a metal alkoxide to form a guanidine compound in which X is a hydroxyl group or an alkoxy group.

Examples of guanidine derivatives of expressed by the formula (I) in accordance with the present invention include the following compounds:

Compound Example

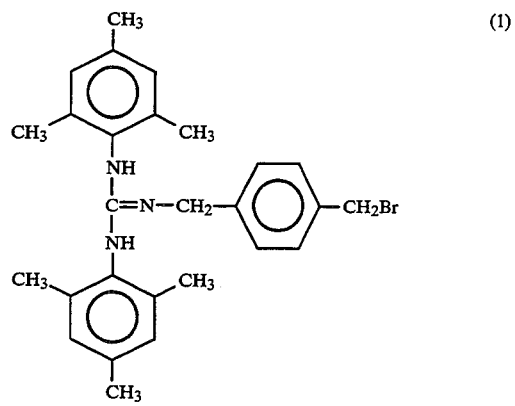

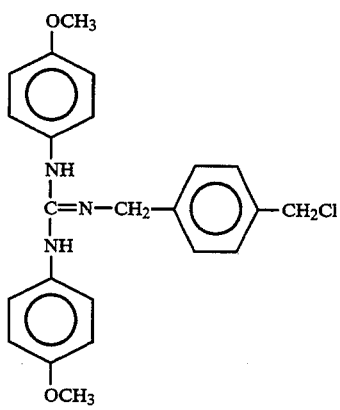 (2)

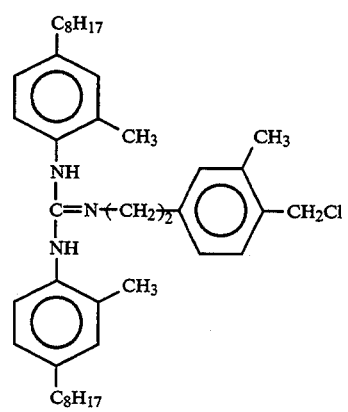 (3)

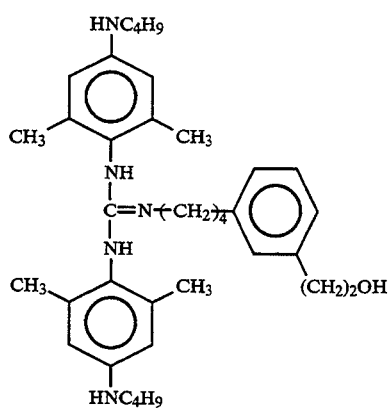 (4)

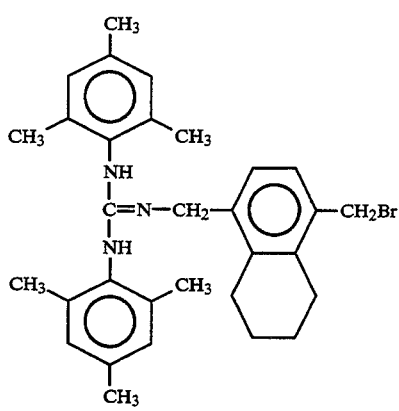 (5)

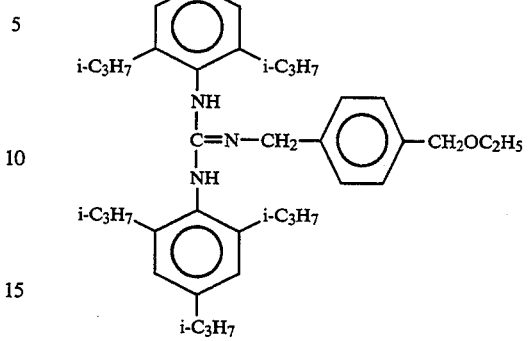 (6)

These compound examples are typical examples selected in view of the ease of the synthesis thereof. The compounds of the present invention are not limited to these compounds.

Of the guanidine compounds expressed by the formula (I) in the present invention, guanidine compounds expressed by the formula (II) are preferable.

Examples of guanidine compounds expressed by the formula (II) include the following compounds:

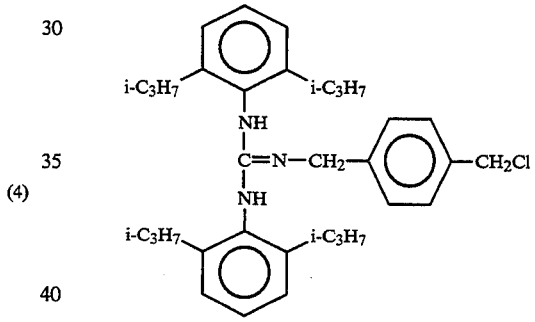 (7)

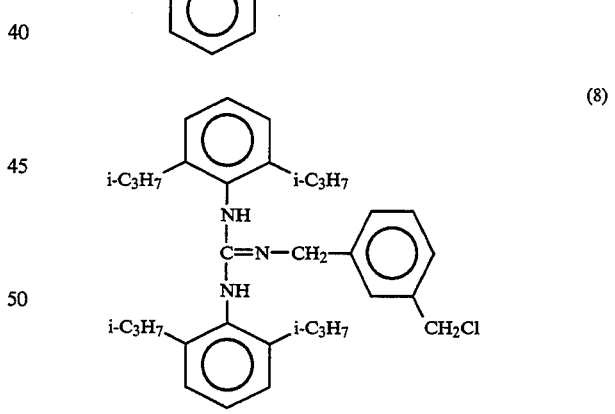 (8)

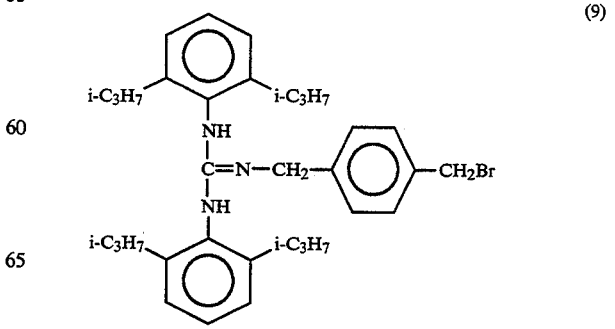 (9)

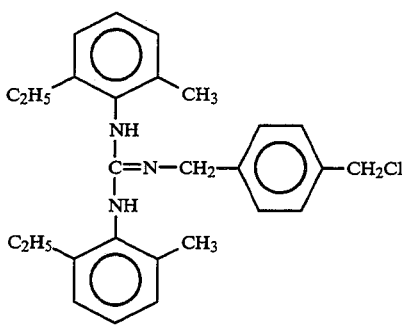

(10)

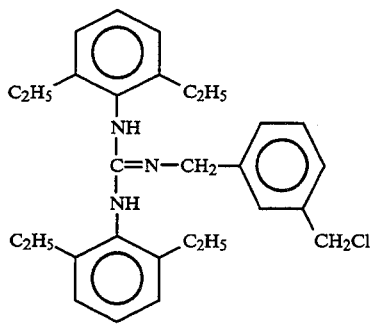

(11)

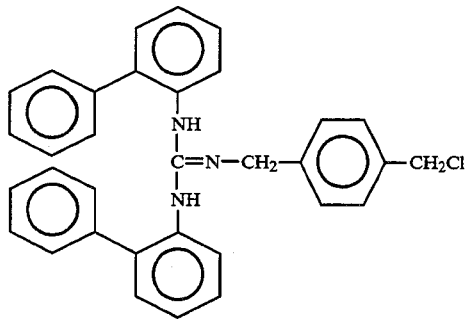

(12)

The above compounds are typical examples of the present invention, and the compounds of the present invention are not limited to these compounds.

Each of the compounds expressed by the formula (II) has as a nucleus substituent a halogenated methyl group having high reactivity, and is thus expected as an intermediate for a compound having the property of being positively charged.

The compounds expressed by the formula (II) can be produced by, for example, a method of reacting equimolar amounts of corresponding N,N'-diarylguanidine and xylylene dihalide in the presence of a base.

The guanidine compounds expressed by the formula (I) or (II) in the present invention are white or light-colored and are thus very useful as charge controlling materials for color toners, without inhibiting the color tone of a coloring material for color toners.

Another characteristic of the present invention is that a guanidine compound expressed by the formula (I) or (II) of the present invention is applied to a toner for developing an electrostatic image.

A guanidine compound of the present invention is contained in a toner by a method of adding it to the inside of the toner or a method of externally adding it to the toner. The amount of the guanidine compound used is determined by the kind of the binder resin used, the presence of the additives added as occasion demands, and the method of producing the toner including the dispersing method, and it is not unconditionally limited. When a guanidine compound is added to the inside of a toner, the amount of the compound used is within the range of 0.1 to 10 parts by weight, preferably 0.1 to 5 parts by weight, relative to 100 parts by weight of the binder resin used. When a guanidine compound is externally added to a toner, the amount of the compound used is preferably 0.01 to 10 parts by weight relative to 100 parts by weight of the resin used. Particularly, a guanidine compound is preferably mechanochemically bonded to the surfaces of the toner particles.

The guanidine compounds used in the present invention can be respectively used in combination with known charge controlling agents.

The toner basically comprises a coloring agent, a binder resin and other additives. The other composition of the toner in accordance with the present invention is described below.

Examples of coloring agents, that are used in the toner of the present invention, include known dyes and pigments such as carbon black, lamp black, iron black, ultramarine, nigrosine dyes, aniline blue, phthalocyanine blue, phthalocyanine green, Hansa yellow G, rhodamine 6G, lake, chalcooil blue, chrome yellow, quinacridone, benzidine yellow, rose bengale, triarylmethane dyes, and monoazo type and disazo type dyes and pigments. These dyes and pigments can be used singly or in a mixture.

Examples of resins, that may be used in the present invention, include styrene and substituted styrene homopolymers such as polystyrene, poly-p-chlorostyrene, polyvinyltoluene; styrene type copolymers such as styrene-p-chlorostyrene copolymers, styrene-vinyltoluene copolymers, styrene-vinylnaphthalene copolymers, styrene-acrylic ester copolymers, styrene-methacrylic ester copolymers, styrene-α-methyl chloromethacrylate copolymers, styrene-acrylonitrile copolymers, styrene-vinyl methyl ether copolymers, styrene-vinyl ethyl ether copolymers, styrene-vinyl methyl ketone copolymers, styrene-butadiene copolymers, styrene-isoprene copolymers, and styrene-acrylonitrile-indene copolymers; phenol resins; natural modified phenol resins; natural resin-modified maleic resins; acrylic resins; methacrylic resins; polyvinyl acetates; silicone resins; polyester resins; polyurethanes; polyamide resins; furan resins; epoxy resins; xylene resins; polyvinyl butyral resins; terpene resins; coumarone-indene resins; and petroleum resins.

Crosslinked styrene copolymers are also preferable binder resins. Examples of comonomers for styrene monomers of styrene copolymers include monocarboxylic acids each having a double bond and substitution products thereof such as acrylic acid, methyl acrylate, ethyl acrylate, butyl acrylate, dodecyl acrylate, octyl acrylate, 2-ethyl hexyl acrylate, phenyl acrylate, methacrylic acid, methyl methacrylate, ethyl methacrylate, butyl methacrylate, octyl methacrylate, acrylonitrile, methacrylonitrile and acrylamide; dicarboxylic acids each having a double bond and substitution products thereof such as maleic acid, butyl maleate, methyl maleate and dimethyl maleate; vinyl esters such as vinyl chloride, vinyl acetate and vinyl benzoate; ethylenic olefins such as ethylene, propylene and butylene; vinyl ketones such as vinyl methyl ketone and vinyl hexyl ketone; and vinyl ethers such as vinyl methyl ether, vinyl ethyl ether and vinyl isobutyl ether. These vinyl monomers are used singly or in combination of two or more monomers.

Derivatives having at least two double bonds, which are polymerizable, are used as crosslinking agents. Examples of crosslinking agents include aromatic divinyl derivatives such as divinylbenzene and divinylnaphthalene; carboxylates each having two double bonds such as ethylene glycol diacrylate, ethylene glycol dimethacrylate and 1,3-butanediol dimethacrylate; divinyl derivatives such as divinyl aniline, divinyl ether, divinyl sulfide, divinyl sulfone; and derivatives each having at least three vinyl groups. These derivatives are used singly or in a mixture.

When a pressure fixing method is used, a binder resin for pressure fixing toners can be used. Examples of such resins include polyethylene, polypropylene, polymethylene, polyurethane elastomer, ethylene-ethyl acrylate copolymers, ethylene-vinyl acetate copolymers, ionomer resins, styrene-butadiene copolymers, styrene-isoprene copolymers, linear saturated polyesters and paraffins.

The toner of the present invention can be used as a magnetic toner when a magnetic material is contained therein. Examples of magnetic materials, that may be contained in the magnetic toner of the present invention, include iron oxides such as magnetite, $\gamma$-iron oxide, ferrite and iron-excess ferrite; metals such as iron, cobalt and nickel; alloys of these metals with metals such as aluminum, cobalt, copper, lead, magnesium, tin, zinc, antimony, beryllium, bismuth, cadmium, calcium, manganese, selenium, titanium, tungsten, vanadium; and mixtures thereof.

These ferromagnetic substances have an average particle size of about 0.1 to 1 $\mu$m, preferably about 0.1 to 0.5 $\mu$m. The amount of the magnetic substance contained in the magnetic toner is 40 to 150 parts by weight relative to 100 parts by weight of the binder resin component used, preferably 60 to 120 parts by weight relative to 100 parts by weight of the resin component used.

The toner of the present invention is used in a mixture with carrier powder when being used in a two-component developer. Any known carriers can be used in the present invention. Examples of such carriers include magnetic powder such as iron powder, ferrite powder and nickel powder; glass beads and glass beads having surfaces which are treated with a resin or the like. Examples of such resins used for treatment include styrene-acrylate copolymers, styrene-methacrylate copolymers, acrylate copolymers, methacrylate copolymers, fluorine-containing resins, silicone resins, polyamide resins, ionomer resins and mixtures thereof.

The toner of the present invention may contain additives, as occasion demands. Examples of such additives include lubricants such as zinc stearate; abrasives such as cerium oxide and silicon carbide; fluidity adding agents such as silica fine powder and aluminum oxide; anticaking agents; and conductivity adding agents such as carbon black and tin oxide.

Fine powder of fluorine-containing polymer such as polyvinylidene fluoride fine powder is also a preferable additive from the view points of its fluidity, abrasive properties and charge stability.

In a preferred form of the present invention, about 0.5 to 5 wt % of wax substance such as low-molecular weight polyethylene, a low-molecular weight polypropylene, microcrystalline wax, carnauba wax, sazol wax or paraffin was is added to the toner for the purpose of improving the mold release properties during heat roll fixing.

The toner in accordance with the present invention is preferably produced by a method in which the above-described toner component materials are sufficiently mixed by using a ball mill or another mixer, sufficiently kneaded by using a heat kneader such as a heat roll kneader or an extruder, solidified by cooling, mechanically ground and then classified. Other methods employed for obtaining the toner are a method of obtaining the toner by dispersing component materials in a solution of a binder resin and then spray drying the thus-formed dispersion; a polymerization method of producing the toner by mixing a constituent monomer of a binder resin with predetermined materials to form an emulsion suspension and then polymerizing the suspension; and a method of producing a micro-capsule toner comprising a core material or a shell material by containing predetermined materials in the core material, the shell material or both the materials. If required, desired additives can be further sufficiently mixed with the toner materials by using a mixer such as Henschel mixer to produce the toner in accordance with the present invention.

The toner of the present invention can be used in any developing methods for developing electrostatic images in electrophotography, electrostatic recording and electrostatic printing.

As described above, the novel guanidine type compounds of the present invention have the satisfactory property of being positively frictionally charged and excellent properties as charge controlling agents for toners.

Since the novel guanidine type compounds of the present invention are colored white or light-colored, they can be used as charge controlling agents which can be used in color toners having the property of being positively charged.

When one of the novel guanidine type compounds of the present invention is contained in a toner, the toner obtained exhibits good preservative stability. The toner of the present invention produces a small change in image quality with an environmental variation and can provide good images under conditions within a wide range.

The novel guanidine type compounds of the present invention have not only the above-described excellent properties as charge controlling agents, which are possessed by conventional guanidine type compounds but also extremely good dispersibility in resins. The guanidine type compounds therefore have a characteristic that conditions for producing the toner can be widely determined.

Since the developer of the present invention comprises a toner containing one of the novel guanidine compounds, it is possible to solve the problems of conventional developers and satisfactorily develop images.

The electrophotographic apparatus and the recording apparatus unit of the present invention are described below with reference to FIG. 1.

The surface of an electrically chargeable photosensitive body 1 is charged is charged with a negative polarity by a primary charging device (charging means) 102. A digital latent image is formed by image scanning the photosensitive body employing a modulated light beam 105, also known as the latent image forming means, slit exposure, apparatus and laser beam scanning exposure apparatus. The latent image formed is developed as a negative image by using a one-component magnetic developer 110 which is held in a developing device (developing means) 109 provided with a magnetic blade 111 and a developing sleeve 104 containing a magnet 114. In a developing section, an alternating current (AC) bias, a pulsatile bias and/or a direct current (DC) bias is applied between the conductive base of the photosensitive body 1 and the developing sleeve 104. When transfer paper P is carried to a transfer section, the developed image (toner image) on the surface of the photosensitive drum 1 is electrostatically transferred to the transfer paper P by charging the transfer paper P from the side opposite to the drum side (rear side) by a secondary charging device (transfer means) 103. The transfer paper P, which is separated from the photosensitive drum 1, is subjected to fixing treatment for fixing the toner image on the transfer paper P by a heating pressure roller fixing device 107.

The one-component developer remaining on the photosensitive drum 1 after the transfer process is removed by a cleaning device (cleaning means) 108 having a cleaning blade. After cleaning, the electrical charge remaining on the electrically chargeable photosensitive drum 1 is neutralized by an erase exposure means 106. The process starting from the charging stage by the primary charging device 102 may be repeated.

The chargeable body (the photosensitive drum) for bearing an electrostatic image has a photosensitive layer and an electrically conductive base and is rotated in the direction shown by the arrow on the photosensitive drum 1 of FIG. 1. The developing sleeve 104 which serves as a toner supporting body and which comprises a non-magnetic cylinder, is rotated so that its surface moves in the same direction as that the surface of the body for holding an electrostatic image in the developing section, the photosensitive drum 1, as indicated by the arrow on the surface of the developing sleeve 104 in FIG. 1. In the non-magnetic cylindrical sleeve 104, a multipolar permanent magnet (a magnet roll) 114 which is a magnetic field generating means, is stationary. The one-component insulating magnetic developer 110 in the developing device 109 is applied to the surface of the non-magnetic cylinder. The toner particles in the developer 110 are provided with, for example, negative triboelectrically induced charges (negative frictional electrification), by the friction of the moving surface of the sleeve 104 and the toner particles. When the iron magnetic doctor blade 111 is disposed close to the surface of the cylinder 104 (at a distance of 50 $\mu$m to 500 $\mu$m) so as to be opposite to one polar position of the multipolar permanent magnet, a developer layer can be controlled to be thin (30 $\mu$m to 300 $\mu$m) and uniform. It is therefore possible to form the thin developer layer having a thickness smaller than the distance between the electrostatic image supporting body 1 and the toner supporting body 104 in a non-contact state. The rotational speed of the toner supporting body 104 is adjusted so that the moving speed of the sleeve surface is substantially equal to or close to the moving speed of the electrostatic image supporting surface. A permanent magnet may be used in place of iron to form a counter magnetic pole as the magnetic doctor blade 111. In the developing section, an AC bias or a pulse bias may be applied between the toner carrying body 104 and the electrostatic image supporting surface by the bias means 112. The AC bias preferably has a frequency f of 200 to 4,000 Hz and a voltage Vpp of 500 to 3,000 V.

During transfer of the toner particles in the developing section, the toner particles are transferred to the electrostatic image side by the electrostatic force of the electrostatic image supporting surface and the function of the ac bias or pulse bias applied.

An elastic blade formed by using an elastic material such as silicone rubber may be used in place of the magnetic doctor blade 111 so that the thickness of the developer layer is controlled by using this elastic blade, and the developer is applied to the developer carriers.

The electrophotographic apparatus may comprises an apparatus unit which is formed by integrally bonding some of the components such as the photosensitive body, the developing means, the cleaning means and so forth and which is detachably provided to the apparatus body. For example, the developing means and the photosensitive body are integrally supported to form the single unit which is detachably provided on the apparatus body by using a guide means such as a rail of the body. In this case, the apparatus unit may be further provided with the charging means and/or the cleaning means.

The body, in this case, also comprises the recording medium handling mechanism, control means, powder supply, and the like.

When the electrophotographic apparatus is used as a copying machine or a printer, light image exposure L is carried out by scanning a laser beam, driving an LED array or driving a liquid crystal shutter array using the reflected light and transmitted light from a document or the signal generated by reading a document.

Figure 2:
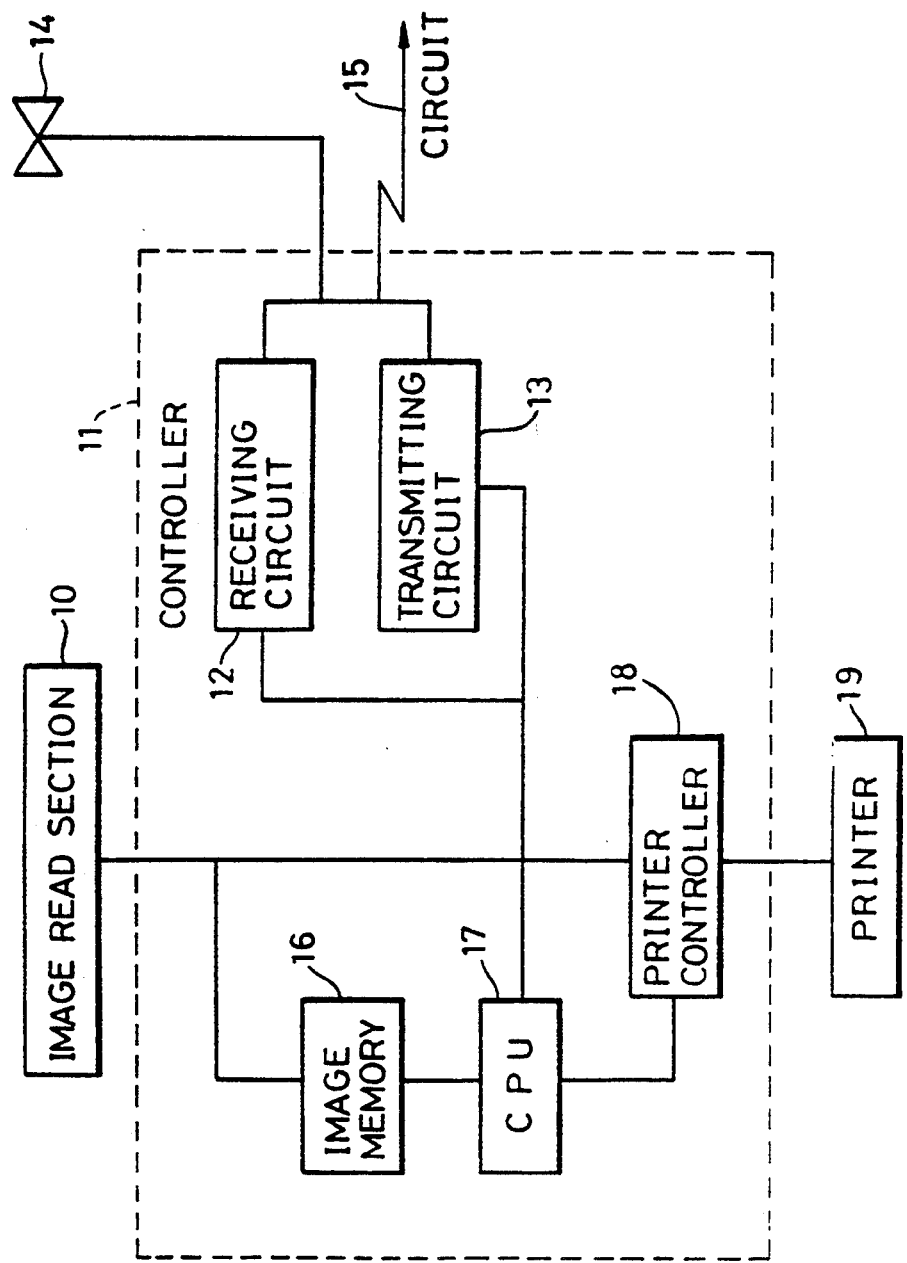
FIG. 2 is a block diagram of a facsimile apparatus which uses as a printer an electrophotographic apparatus.

When the electrophotographic apparatus is used as a printer for a facsimile, light image exposure L is performed for printing the received data. FIG. 2 is a block diagram of an example of this case.

A controller 11 controls an image read section 10 and a printer 119. The whole of the controller is controlled by CPU 17. The read data obtained from the image read section 10 is transmitted to a distant station through a transmitting circuit 13. The data received from the distant station is sent to the printer through a receiving circuit 12. Predetermined image data is stored in an image memory. A printer controller 18 controls the printer. Reference numeral 14 denotes a telephone.

The image (the image information from a remote terminal connected through a circuit) received from a circuit 15 is demodulated by the receiving circuit 12, subjected to decoding by the CPU 17 and then stored in turn in the image memory 16. When at least one page of image is stored in the memory 16, the image on the page is recorded. The CPU 17 reads the image information on the page from the memory 16, decodes the information and then sends the information on the page to the printer controller 18. When the printer controller 18 receives the image information on the page from the CPU 17, the controller 18 controls the printer 19 so that the image information on the page is recorded.

During recording by the printer 19, the CPU 17 receives information on the next page.

In this way, images are received and recorded.

As described above, in the electrophotographic apparatus of the present invention, since the developing means for developing an electrostatic image holds at least the toner containing one of the novel guanidine compounds of the present invention, it produces only a small change in the image formed with an environmental variation and permits the formation of a good image under various conditions.

In the apparatus unit of the present invention, since the developing means, which is supported integrally with the body to be charged to form the unit, holds at least the toner containing one of the guanidine compounds of the present invention, it produces only a small change in the image formed with an environmental variation and permits the formation of a good image under various conditions.

In the facsimile apparatus of the present invention, since the developing means for developing the electrostatic image obtained by the electrophotographic apparatus used as a printer holds at least the toner containing one of the guanidine compounds of the present invention, it produces only a small change in the image formed with an environmental variation and permits the formation of a good image under various conditions.

EXAMPLES

Although the present invention is described in detail below with reference to examples, the invention is not limited to the examples. All the units "parts" described below in composition are "parts by weight".

EXAMPLE 1

Synthesis of N,N'-bis-(2,6-diisopropylphenyl)-N''-(4-chloromethylphenyl) methylguanidine (Compound Example 7)

11.4 g (0.03 mole) of N,N'-bis-(2,6-diisopropylphenyl) guanidine, 5.7 g (0.033 mole) of $\alpha,\alpha$-dichloro-p-xylene and 2.1 g (0.015 mole) of anhydrous potassium carbonate were added to 50 ml of xylene. The thus-formed mixture was then refluxed under heating for 10 hours. After the mixture had been allowed to cool, the insoluble substance was removed by filtration. The thus-obtained filtrate was washed with water and then concentrated for the purpose of recovering the solvent and unreacted raw materials to obtain a slightly yellow crystal. The crystal was then recrystallized from benzene to obtain 6.3 g of white powder.

Melting point: 197.0°–201.0° C.

$H^1$-NMR (CDCl$_3$) δ: 0.8–1.4 (24H, m, CH$_3$), 2.8–3.5 (4H, m, CH), 3.5 (2H, s, NH), 4.49 (2H, s, Cl—CH$_2$), 5.00 (2H, s, N-CH$_2$), 6.95–7.55 (10H, m, Arom-H)

IR $V_{max}^{Nujol}$ cm$^{-1}$:3508, 3400 (N—H), 1630 (C=N)

EXAMPLE 2

Synthesis of N,N'-bis-(2,6-diisopropylphenyl)—N''-(3-chloromethylphenyl) methylguanidine (Compound Example 8)

11.4 g (0.03 mole) of N,N'-bis-(2,6-diisopropylphenyl) guanidine, 5.7 g (0.033 mole) of $\alpha,\alpha$-dichloro-m-xylene and 2.1 g (0.015 mole) of anhydrous potassium carbonate were added to 50 ml of xylene. The thus-formed mixture was then refluxed under heating for 10 hours. After the mixture had been allowed to cool, the insoluble substance was removed by filtration. The thus-obtained filtrate was washed with water and then concentrated for the purpose of recovering the solvent and unreacted raw materials to obtain a slightly yellow crystal. The crystal was then recrystallized from acetone to obtain 5.1 g of white powder.

Melting point: 121.5°–124.0° C.

$H^1$-NMR (CDCl$_3$) δ: 0.8–1.4 (24H, m, CH$_3$), 2.8–3.5 (4H, m, CH), 3.50 (2H, s, NH), 4.51 (2H, s, Cl—CH$_2$), 5.05 (2H, s, N-CH$_2$), 6.95–7.75 (10H, m, Arom-H)

IR $\nu_{max}^{Nujol}$ cm$^{-1}$: 3490, 3375 (N—H), 1630 (C=N)

EXAMPLE 3

Synthesis of N,N'-bis-(2,6-diisopropylphenyl)—N''-(4-bromomethylphenyl) methylguanidine (Compound Example 9)

11.4 g (0.03 mole) of N,N'-bis-(2,6-diisopropylphenyl) guanidine, 8.7 g (0.033 mole) of $\alpha,\alpha$-dibromo-p-xylene and 2.1 g (0.015 mole) of anhydrous potassium carbonate were added to 50 ml of toluene. The thus-formed mixture was then refluxed under heating for 10 hours. After the mixture had been allowed to cool, the insoluble substance was removed by filtration. The thus-obtained filtrate was washed with water and then concentrated for the purpose of recovering the solvent to obtain a slightly brown powder. The powder was then recrystallized from acetone to obtain 6.6 g of white powder.

Melting point: 208.0°–214.0° C.

$H^1$-NMR (CDCl$_3$) δ: 0.7–1.4 (24H, m, CH$_3$), 2.8–3.5 (4H, m, CH), 3.50 (2H, s, NH), 4.41 (2H, s, Cl—CH$_2$), 5.00 (2H, s, N-CH$_2$), 6.95–7.50 (10H, m, Arom-H)

IR $\nu_{max}^{Nujol}$ cm$^{-1}$: 3508, 3400 (N—H), 1628 (C=N)

EXAMPLE 4

Synthesis of N,N'-bis-(2,6-diethylphenyl)—N''-(3-chloromethylphenyl) methylguanidine (Compound Example 11)

9.7 g (0.03 mole) of N,N'-bis-(2,6-diethylphenyl) guanidine, 5.7 g (0.033 mole) of $\alpha,\alpha$-dichloro-m-xylene and 2.1 g (0.015 mole) of anhydrous potassium carbonate were added to 50 ml of toluene. The thus-formed mixture was then refluxed under heating for 10 hours. After the mixture had been allowed to cool, the insoluble substance was removed by filtration. The thus-obtained filtrate was washed with water and then concentrated for the purpose of recovering the solvent and unreacted raw materials to obtain a slightly yellow crystal. The crystal was then recrystallized from benzene to obtain 4.5 g of white powder.

Melting point: 83.5°–86.5° C.

$H^1$-NMR (CDCl$_3$) δ: 0.85–1.40 (12H, m, CH$_3$), 2.15–2.85 (8H, m, CH$_3$), 3.42 (2H, s, NH), 4.48 (2H, s, Cl—CH$_2$), 4.96 (2H, s, N-CH$_2$), 6.87–7.52 (10H, m, Arom-H)

IR $\nu_{max}^{Nujol}$ cm$^{-1}$: 3468, 3364 (N—H), 1634 (C=N)

EXAMPLE 5

Synthesis of N,N'-bis-(2-phenylphenyl)—N''-(4-chloromethylphenyl) methylguanidine (Compound Example 12)

10.9 g (0.03 mole) of N,N'-bis-(2-phenylphenyl) guanidine, 5.7 g (0.033 mole) of $\alpha,\alpha$-dichloro-p-xylene and 2.1 g (0.015 mole) of anhydrous potassium carbonate were added to 50 ml of toluene. The thus-formed mixture was then refluxed under heating for 10 hours. After the mixture had been allowed to cool, the insoluble substance was removed by filtration. The thus-obtained filtrate was washed with water and then concentrated for the purpose of recovering the solvent and unreacted raw materials to obtain a slightly brown powder. The powder was then recrystallized from acetone to obtain 3.1 g of white powder.

Melting point: 87.0°–91.5° C.

$H^1$-NMR (CDCl$_3$) δ: 3.35 (2H, s, NH), 4.55 (2H, s, Cl—CH$_2$), 5.10 (2H, s, N-CH$_2$), 6.65–7.45 (22H, m, Arom-H)

IR $v_{max}^{Nujol}$ cm$^{-}$: 3465, 3375 (N-H), 1650 (C=N)

EXAMPLE 6

| Styrene/n-butyl methacryate copolymer (copolymerization ratio by weight, 80/20; weight average molecular weight, 300,000) | 100 parts |
| --- | --- |
| Carbon black | 5 parts |
| Compound Example | 2 parts |

The above materials were well mixed by using a blender and then kneaded by using a biaxial kneading extruder set at 150° C. The thus-obtained kneaded product was cooled, roughly ground by using a cutter mill and then finely ground by using a pulverizer which employed a jet air flow. The thus-obtained finely ground powder was classified by using a fixed-wall type pneumatic classifier.

The thus-obtained powder fraction was further classified by using a multi-division classifier (Erbojet classifier manufactured by Nittetsu Kogyo K. K. ) which employed the Coanda effect in order to simultaneously precisely remove superfines to obtain a fine powder (toner) having a weight average particle size of 10.5 μm.

0.4 part of hydrophobic dry silica (BET specific surface area, 200 m²/g) having the property of being positively charged and which is treated with silicone oil having amino group was added to 100 parts of the obtained toner. The thus-obtained mixture was then mixed by using a Henschel mixer to prepare a black toner which has the property of being positively charged and which has the hydrophobic dry silica having the property of being positively charged on the toner particle surfaces.

9 parts of the thus-obtained toner was mixed with 100 parts of acrylic coat ferrite carriers having an average particle size of 65 μm to form a two-component developer.

Copying tests of the thus-formed two-component developer were made by using a modified machine of a color electrophotographic copying machine CLC-1 (Canon Co., Ltd.), which is commercially available, in which the OPC photosensitive drum was replaced by an amorphous silicone drum.

As a result, a clear black image having a density of 1.37 can be obtained from the initial stage under the environmental conditions of 23° C. and 60%, and no deterioration in image quality was observed after images had been copied on 20,000 sheets of paper.

As a result of copying tests under the environmental conditions of 15° C. and 10%, an image having a density of as high as 1.33 could be obtained from the initial stage. In addition, under the environmental conditions off 32° C. and 85%, good images with a density of 1.42 could be obtained.

EXAMPLE 7

A fine powder (toner) having a weight average particle size of 11.3 μm was obtained by the same method as that employed in Example 6 except that 5 parts of carbon black used in Example 6 was replaced by 3 parts of quinacridone pigment (C. I. Pigment Red 122). Silica was then mixed with the fine powder by the same method as that employed in Example 6 to prepare a magenta toner which had the property of being positively charged and which contained hydrophobic dry silica having the property of being positively charged on the toner particle surfaces.

The same carriers as those used in Example 6 were mixed with the toner in the same ratio to form a two-component developer.

Copying tests of the thus-formed two-component developer were made by the same method as that employed in Example 6. As a result, under the environmental conditions of 23° C. and 60%, a magenta image having a density of 1.35 could be obtained from the initial stage. No deterioration in image quality was observed after images had been copied on 20,000 sheets of paper.

As a result of copying tests under the environmental conditions of 35° C., 85% and 15° C., 10%, good results were obtained in the same way as in the case of the conditions of 23° C. and 60%.

EXAMPLE 8

A fine powder (toner) having a weight average particle size of 10.9 μm was obtained by the same method as that employed in Example 6 except that 5 parts of carbon black used in Example 6 was replaced by 3 parts of C. I. Pigment Yellow 17. Silica was then mixed with the toner obtained by the same method as in Example 6 to prepare a yellow toner having the property of being positively charged and having hydrophobic dry silica having the property of being positively charged on the toner particle surfaces.

The same carriers as those used in Example 6 were mixed with the thus-prepared toner in the same ratio to form a two-component developer.

The copying tests of the two-component developer were made by the same method as that employed in Example 6. As a result, under the environmental conditions of 23° C. and 60%, a clear yellow image having a density of 1.36 could be obtained from the initial stage. No deterioration in image quality was observed after images had been copied on 20,000 sheets of paper.

As a result of copying tests under the environmental conditions of 35° C., 85% and 15° C., 10%, good results could be obtained in the same way as in the case of the conditions of 23° C. and 60%.

EXAMPLE 9

A fine powder (toner) having a weight average particle size of 11.0 μm was obtained by the same method as that employed in Example 6 except that 5 parts of carbon black used in Example 6 was replaced by 5 parts of copper phthalocyanine pigment (C. I. pigment blue 15). Silica was then mixed with the toner obtained by the same method as in Example 6 to prepare a yellow toner having the property of being positively charged and having hydrophobic dry silica having the property of being positively charged on the toner particle surfaces.

The same carriers as those used in Example 6 were mixed with the thus-prepared toner in the same ratio to form a two-component developer.

The copying tests of the two-component developer were made by the same method as that employed in Example 6. As a result, under the environmental conditions of 23° C. and 60%, a clear yellow image having a density of 1.37 could be obtained from the initial stage. No deterioration in image quality was observed after images had been copied on 20,000 sheets of paper.

As a result of copying tests under the environmental conditions of 35° C., 85% and 15° C., 10%, good results could be obtained in the same way as in the case of the conditions of 23° C. and 60%.

EXAMPLE 10

A full color image was formed by using the cyan, magenta, yellow and black two-component developers used in Examples 6 to 9. As a result, a clear full color image having excellent color mixture and gradation was obtained.

EXAMPLE 11

| | |
|---|---|
| Styrene/n-butyl methacrylate copolymer (copolymerization ratio 80/20, weight average molecular weight 300,000) | 100 parts |
| 2,9-dimethylquinacridone pigment | 5 parts |
| Low-molecular weight polypropylene wax | 3 parts |
| Compound Example 8 | 2 parts |

The above materials were well mixed by using a blender and then kneaded by using a biaxial kneading extruder. The kneading temperature was set to 100° C., which was optimum in view of the dispersibility of the pigment. The thus-obtained kneaded product was then cooled, roughly ground by using a cutter mill and then finely ground by using a pulverizer which employed a jet air flow. The thus-obtained finely ground powder was then classified by using a fixed-wall type pneumatic classifier.

In order to simultaneously precisely remove superfines, the thus-obtained powder fraction was further classified by using a multi-division classifier (an erbojet classifier manufactured by Nittetsu Kogyo K. K.) which employed the Coanda effect to obtain a fine powder (toner) having a weight average particle size of 11.3 μm.

0.5 parts of hydrophobic dry silica (BET specific surface area 130 m$^2$/g) which had the property of being positively charged and which was treated with silicone oil having amino groups, was added to 100 parts of the fine powder obtained. The thus-obtained mixture was then mixed by using a Henschel mixer to prepare a magenta toner having the property of being positively charged and having hydrophobic dry silica having the property of being positively charged, on the toner particle surfaces.

10 parts of the thus-obtained toner was mixed with 100 parts of fluorine-acrylic coat ferrite carrier having an average particle size of 65 μm to form a two-component developer.

Copying tests of the thus-formed two-component developer were made by using a copying machine (trade name, NP-5540 manufactured by Canon Inc.), which was commercially available, under the environmental conditions of 23° C. and 60%. As a result, a magenta image of good quality having a density of 1.33 could be obtained. As a result of durability test performed by continuously copying images on 4000 sheets of paper using the developer, the good images obtained were by no means inferior to the image obtained in the early stage.

As a result of copying tests under the conditions of 15° C., 10% and 35° C., 83%, the same good results were obtained.

COMPARATIVE EXAMPLE 1

Materials were kneaded by the same method as that employed in Example 11 using a kneader set at 100° C. except that 2 parts of Compound Example 8 used in Example 11 was replaced by 2 parts of N,N'-bis(-paramethoxylphenyl)N''-benzylguanidine, which was generally known, to form a fine powder (toner) having a weight average particle size of 11.6 μm. Silica was mixed with the thus-formed silica in the same way as that employed in Example 11 to prepare a magenta toner which had the property of being positively charged and which contained the hydrophobic dry silica having the property of being positively charged on the toner particle surfaces.

10 parts of the thus-obtained toner was mixed with 100 parts of fluorine-acrylic coat ferrite carriers having an average particle size of 65 μm to form a two-component developer.

Copying tests of the thus-formed two-component developer were made by using a copying machine (trade name, NP-5540 manufactured by Canon Inc.), which was commercially available, under the conditions of 23° C. and 60%. As a result, magenta images of good quality having a density of 1.31 were obtained. When the durability was examined by continuously copying images on 40000 sheets of paper using the developer, the good images obtained were good and by no means inferior to the image obtained in the initial stage.

As result of copying tests under the environmental conditions of 15° C. and 10%, although an image of good quality was obtained from the initial stage, fogging was observed in the non-image portions of the images obtained, which had substantially the same density as that in the initial state, after images had been continuously copied on 1000 sheets of paper.

Further, as a result of copying tests under the environmental conditions of 35° C. and 85%, although an image of good quality was obtained in the initial stage, slight fogging was observed on the backgrounds after images had been continuously copied on 1000 sheets of paper. It is thought that the fogging occurred owing to the poor dispersibility of the charge controlling agent used, which was caused by the absence of the group X therein, the group being present in the formula (I) or (II) of the guanidine compounds of the present invention.

EXAMPLE 12

| | |
|---|---|
| Styrene/n-butyl methacrylate/ divinylbenzene copolymer (copolymerization ratio, 85/15/0.5 weight average molecular weight, 300,000) | 100 parts |
| Magnetic substance | 80 parts |
| Low-molecular weight polypropylene wax | 3 parts |
| Compound Example 7 | 3 parts |

The above materials were well mixed by using a blender and then kneaded by using a biaxial kneading extruder set at 170° C. The thus-obtained kneaded product was then cooled, roughly ground by using a cutter mill and then finely ground by using a purverizer, which employed a jet air flow. The thus-obtained finely ground powder was classified by using a fixed-wall type pneumatic classifier.

In order to simultaneously precisely remove superfines, the thus-obtained powder faction was further classified by using a multi-division classifier (an erbojet classifier manufactured by Nittetsu Kogyo K. K.), which employed the Coanda effect, to obtain a fine powder (toner) having a weight average particle size of 8.9 μm.

0.6 part of hydrophobic dry silica (BET specific surface area, 130 m²/g) having the property of being positively charged, which was treated with silicone oil having amino groups, was added to 100 parts of the obtained toner. The resultant mixture was then mixed by using a Henschel mixer to prepare a magnetic black toner which had the property of being positively charged and which had the hydrophobic dry silica on the toner particle surfaces.

Copying tests were made by applying the obtained magnetic toner to a copying machine (trade name, NP-4835 manufactured by Canon Inc.), which was commercially available, under the environmental conditions of 23° C. and 60%. As a result, clear black images having a density of 1.35 and neither fog nor roughness were obtained.

When the durability of the magnetic toner was examined by continuously copying images on 30,000 sheets of paper, the images obtained were good and by no means inferior to the images obtained in the early stage. As a result of measurement of the frictional charge amount of the toner supported on the developing sleeve, the amount was +9.3 μc/g in the early stage and +8.9 μc/g after images had been copied on 30,000 sheets of paper, which were satisfactorily high values. The sleeve was hardly soiled.

As a result of copying tests under the conditions of 15° C. and 10%, images having a high density was obtained. When the durability of the magnetic toner was examined by continuously copying images on 30,000 sheets of paper, images of good quality having a high density were obtained.

When copying tests were made under the harsh conditions of 45° C. and 95%, good results were obtained.

Further, when the magnetic toner was allowed to stand for 1 month under the harsh conditions and then subjected to copying tests, satisfactory results without any problem were obtained.

EXAMPLE 13

A fine powder (toner) having a weight average particle size of 8.6 μm was obtained by the same method as that employed in Example 12 except that 3 parts of Compound Example 7 used in Example 12 was replaced by 5 parts of Compound Example 9. Silica was mixed with the thus-formed toner in the same way as that employed in Example 12 to prepare a magnetic black toner having the property of being positively charged, which had the hydrophobic dry silica having the property of being positively charged on the toner particle surfaces.

When copying tests were made by applying the thus-formed magnetic toner to a copying machine (trace name, NP-1215 manufactured by Canon Inc.), which was commercially available, under the environmental conditions of 23° C. and 60%, clear black images having a density of 1.36 and neither fog nor roughness were obtained.

When the durability was examined by continuously copying images on 20,000 sheets of paper, the images obtained were good and by no means inferior to the images obtained at the initial stage.

Further, as a result of copying tests made under the conditions of environmental conditions of 15° C. and 10%, the images obtained had a high density and good quality. As a result of 2000 times of continuous copying tests, the same good results were obtained.

When copying tests were made under the environmental conditions of 35° C. and 85%, good results were obtained.

Further, when the magnetic toner was allowed to stand for 1 month under the same environmental conditions and then subjected to copying tests, satisfactory results having no problem were obtained.

EXAMPLE 14

| | |
|---|---|
| Styrene/n-butyl methacrylate/acrylic acid copolymer (copolymerizatio ratio, 84/15/1 weight average molecular weight, 250,000) | 100 parts |
| Magnetic subsance | 60 parts |
| Low-molecular weight polypropylene wax | 3 parts |
| Compound Example 8 | 2 parts |

The above materials were well mixed by using a blender and then kneaded by using a biaxial kneading extruder set at 130° C. The thus-obtained kneaded product was then cooled, roughly ground by using a cutter mill and then finely ground by using a purverizer, which employed a jet air flow. The thus-obtained finely ground powder was classified by using a fixed-wall type pneumatic classifier.

In order to simultaneously precisely remove superfines, the thus-obtained powder faction was further classified by using a multi-division classifier (an erbojet classifier manufactured by Nittetsu Kogyo K. K.), which employed the Coanda effect, to obtain a fine powder (toner) having a weight average particle size of 11.7 μm.

0.8 part of hydrophobic dry silica (BET specific surface area, 200 m²/g) having the property of being positively charged, which was treated with dimethylaminopropyl trimethoxysilane, was added to 100 parts of the obtained toner. The resultant mixture was then mixed by using a Henschel mixer to prepare a magnetic black toner which had the property of being positively charged and which had the hydrophobic dry silica on the toner particle surfaces.

Copying tests were made by applying the obtained magnetic toner to a copying machine (trade name, NP-5540 manufactured by Canon Inc.), which was commercially available, under the environmental conditions of 23° C. and 60%. As a result, clear black images having a density of 1.30 and high quality were obtained.

When the durability of the magnetic toner was examined by continuously copying images on 20,000 sheets of paper, the images obtained were good and by no means inferior to the images obtained in the early stage.

As a result of copying tests under the conditions of 15° C., and 10% and 35° C., 83%, good results were obtained.

EXAMPLE 15

| | |
|---|---|
| Polyester (acid value, 1 mg KOH/g; hydroxyl value, 18 mg KOH/g) | 100 parts |
| Magnetic substance | 60 parts |
| Low-molecular weight polypropylene wax | 3 parts |
| Compound Example 11 | 4 parts |

The above materials were well mixed by using a blender and then kneaded by using a biaxial kneading extruder set at 140° C. The thus-obtained kneaded product was then cooled, roughly ground by using a cutter mill and then finely ground by using a purverizer, which employed a jet air flow. The thus-obtained finely ground powder was classified by using a fixed-wall type pneumatic classifier.

In order to simultaneously precisely remove superfines, the thus-obtained powder faction was further classified by using a multi-division classifier (an erbojet classifier manufactured by Nittetsu Kogyo K. K.), which employed the Coanda effect, to obtain a fine powder (toner) having a weight average particle size of 12.6 μm.

0.8 part of hydrophobic dry silica (BET specific surface area, 200 m²/g) having the property of being positively charged, which was treated with silicone oil having amino groups, was added to 100 parts of the obtained toner. The resultant mixture was then mixed by using a Henschel mixer to prepare a magnetic black toner which had the property of being positively charged and which had the hydrophobic dry silica on the toner particle surfaces.

Copying tests were made by applying the obtained magnetic toner to a copying machine (trade name, NP-5540 manufactured by Canon Inc.), which was commercially available, under the environmental conditions of 23° C. and 60%. As a result, clear black images having a density of 1.33 and high quality were obtained.

When the durability of the magnetic toner was examined by continuously copying images on 10,000 sheets of paper, the images obtained were good and by no means inferior to the images obtained in the early stage.

As a result of copying tests under the conditions of 15° C., 10% and 35° C., 83%, good results were obtained.

COMPARATIVE EXAMPLE 2

A fine powder (toner) having a weight average particle size 8.6 μm was obtained by mixing, kneading, grinding and classification by the same method as that employed in Example 12 except that 3 parts of Compound Example 1 used in Example 12 was replaced by 3 parts of N,N'-bis(3-methylphenyl) guanidine. Silica was then mixed with the thus-obtained toner by the same method as that employed in Example 12 to prepare a magnetic black toner having the property of being positively charged, which had hydrophobic dry silica having the property of being positively charged on the toner particle surfaces.

Copying tests were made by applying the obtained magnetic toner to a copying machine (trade name, NP-4835 manufactured by Canon Inc.), which was commercially available, under the environmental conditions of 23° C. and 60%. As a result, clear black images having a density of 1.31 and neither fog nor roughness were obtained.

When the durability of the magnetic toner was examined by continuously copying images on 30,000 sheets of paper, the images obtained were by no means inferior to the images obtained in the early stage. As a result of measurement of the frictional charge amount of the toner supported on the developing sleeve, the amount was +7.8 μc/g in the early stage and +7.1 μc/g after images had been copied on 30,000 sheets of paper, which were lower than the values obtained in Example 12. The sleeve was hardly soiled.

As a result of copying tests under the environmental conditions of 15° C. and 10%, images having a high density were obtained. When the durability of the magnetic toner was examined by continuously copying images on 30,000 sheets of paper, images having a high density and high quality were obtained.

As a result of copying test under the harsh environmental conditions of 45° C. and 95%, a reduction in image density was observed after about 20,000 durability tests.

What is claimed is:

1. An image forming method comprising the steps of:
   charging a chargeable body by a charging means;
   forming an electrophotographic latent image on said chargeable body by a latent image forming means, and
   developing said electrophotographic latent image by a developer, wherein said developer includes a toner comprising a binder resin and a guanidine type compound having the following formula:

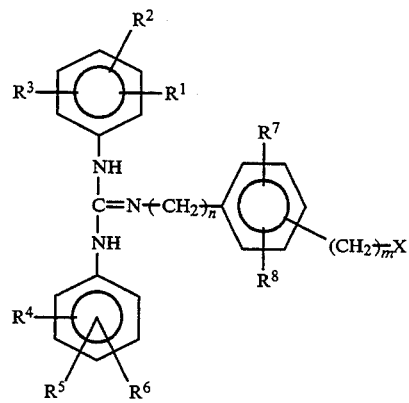

wherein $R^1$ to $R^8$ are each a hydrogen atom, an alkyl group having from 1 to 18 carbon atoms, a substituted or unsubstituted phenyl group, a substituted or unsubstituted naphthyl group, a substituted or unsubstituted tolyl group or a substituted or unsubstituted xylyl group; $R^1$ to $R^8$ are the same or different and together form a ring with adjacent substituents; X is a halogen atom, an hydroxyl group or an alkoxy group; and m and n are each an integer having a value of 1 to 8.

2. The method according to claim 1, wherein said guanidine type compound has the following formula:

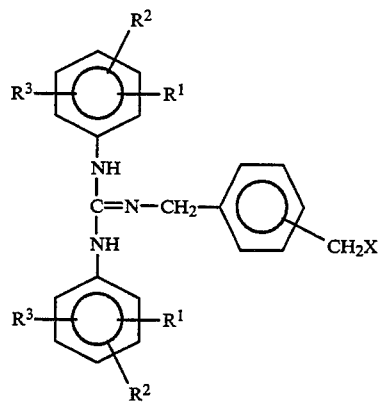

wherein $R^1$, $R^2$, $R^3$ are each a hydrogen atom, an alkyl group having from 1 to 4 carbon atoms or a phenyl group; $R^1$, $R^2$, $R^3$ are the same or different and together form a ring with adjacent substituents; and X is a halogen atom.

3. The method according to claim 2, wherein said toner includes a silica powder.

4. The method according to claim 3, wherein said silica powder consists of silica which is a positively chargeable silica.

5. The method according to claim 4, wherein said positively chargeable silica is hydrophobic dry silica treated with silicone oil having amino groups.

6. The method according to claim 5, wherein at least one of substituents $R^1$, $R^2$, $R^3$, $R^4$, $R^5$ and $R^6$ is selected from the group consisting of an alkyl group and a phenyl group, and the remaining substituents are hydrogen atoms.

7. The method according to claim 6, wherein said alkyl group or phenyl group is at the ortho-position.

8. The method according to claim 2, wherein said toner is a magnetic toner containing a magnetic material.

9. The method according to claim 2, wherein said binder is a polystyrene homopolymer or copolymer resin.

10. The method according to claim 2, wherein said binder resin is a polyethylene homopolymer or copolymer resin.

11. The method according to claim 2, wherein at least one of $R^1$, $R^2$, and $R^3$ is selected from the group consisting of an alkyl group and a phenyl group.

12. The method according to claim 2, wherein at least two of $R^1$, $R^2$, and $R^3$ are selected from the group consisting of an alkyl group and a phenyl group.

13. The method according to claim 12, wherein at least one of substituents $R^1$, $R^2$ and $R^3$ is selected from the group consisting of an alkyl group and a phenyl group, and the remaining substituents are hydrogen atoms.

14. The method according to claim 12, wherein an alkyl group or phenyl group is at the orthoposition.

15. The method according to claim 2, wherein $R^1$, $R^2$ and $R^3$ are each alkyl groups.

16. The method according to claim 15, wherein $R^1$, $R^2$ and $R^3$ are each the same alkyl group.

17. The method according to claim 1, wherein said toner is mixed with a silica powder.

18. The method according to claim 17, wherein said silica powder is a positively chargeable silica.

19. The method according to claim 18, wherein said positively chargeable silica is hydrophobic dry silica treated with silicone oil having amino groups.

20. The method according to claim 1, wherein said toner is a magnetic toner containing a magnetic material.

21. The method according to claim 1, wherein said binder is a polystyrene homopolymer or copolymer resin.

22. The method according to claim 1, wherein said binder resin is a polyethylene homopolymer or copolymer resin.

23. The method according to claim 1, wherein X is selected from the group consisting of chlorine and bromine.

24. The method according to claim 1, wherein at least one of $R^1$, $R^2$, $R^3$, $R^4$, $R^5$ and $R^6$ is selected from the group consisting of an alkyl group and a phenyl group.

25. The method according to claim 1, wherein at least two of $R^1$, $R^2$, $R^3$, $R^4$, $R^5$ and $R^6$ are selected from the group consisting of an alkyl group and a phenyl group.

26. The method according to claim 1, wherein $R^1$, $R^2$, $R^3$, $R^4$, $R^5$ and $R^6$ are each alkyl groups.

27. The method according to claim 26, wherein $R^1$, $R^2$, $R^3$, $R^4$, $R^5$ and $R^6$ are each the same alkyl group.

* * * * *